United States Patent
Filbert et al.

(10) Patent No.: US 6,211,230 B1
(45) Date of Patent: Apr. 3, 2001

(54) METHOD OF REDUCING BRAIN DAMAGE RESULTING FROM SEIZURES

(75) Inventors: Margaret Gillespie Filbert, Ellicott City, MD (US); Gerald Paul Harding Ballough, Drexel Hill, PA (US)

(73) Assignee: The United States of America as represented by the Secretary of the Army, Washington, DC (US)

(*) Notice: Subject to any disclaimer, the term of this patent is extended or adjusted under 35 U.S.C. 154(b) by 0 days.

(21) Appl. No.: 09/487,704

(22) Filed: Jan. 19, 2000

Related U.S. Application Data

(60) Provisional application No. 60/155,774, filed on Sep. 27, 1999.

(51) Int. Cl.[7] .......................... A61K 31/35; A61K 31/66
(52) U.S. Cl. ................................ 514/454; 514/75
(58) Field of Search ........................ 514/454, 75

(56) References Cited

PUBLICATIONS

Filbert et al.; "Neuroprotective effects of HU–211 on brain damage resulting from soman–induced seizures"; Society for Neuroscience Abstracts, (1998) vol. 24, No. 1–2, pp. 1938. Meeting Info.: 28th Annual Meeting of the Society for Neuroscience, Part, 1998.*

Feigenbaum J., Bergmann F., Richmond S., Mechoulam R., Nadler V., Kloog Y. and Sokolovsky M. (1989) Nonpsychotropic cannabanoid acts as a functional N–methyl–D–aspartate receptor blocker. *Proc. Natl. Acad. Sci. USA* 86, pp. 9584–9587.

Shohami E., Novikov M. and Mechoulam R. (1993) A Nonpsychotropic Cannaboid, HU–211, Has Cerebroprotective Effects After Closed Head Injury in the Rat. *J of Neurotrauma* 10, pp. 109–119.

Nadler V., Mechoulam R. and Sokolovsky M. (1993) Blockade of $^{45}Ca^{2+}$ influx through the N–methyl–D–asparate receptor ion channel by the non–psychoactive cannaboid HU–211. *Brain Res* 622, pp. 79–85.

Streim S., Bar–Joseph A., Berkovitch Y. and Biegon A. (1997) Interaction of Dexanabinol (HU–211), a novel NMDA receptor antagonist, with the dopaminergic system. *Eur J Pharmacol* 338, pp. 205–213.

Belayev L., Busto R., Watson B. and Ginsberg M. (1995) Post–ischemic administration of HU–211, a novel non–competitive NMDA antagonist, protects against blood–barrier disruption in photochemical cortical infarction in rats: a quantitative study. *Brain Res* 702, pp. 266–270.

Shohami E., Novikov M.and Bass R. (1995) Long–term effect of HU–211, a novel non–competitive NMDA antagonist, on motor and memory functions after closed head injury in the rat. *Brain Res* 674, pp. 55–62.

Nadler V., Biegon A, Beit–Yanni E., Adamchik J and Shohami E., (1995) Ca accumulation in rat brain after closed head injury: attenuation by the novel neuroprotective agent HU–211. *Brain Res* 685, pp. 1–11.

Brewster M.E., Pop E., Foltz R.L., Reuschel S., Griffith W., Amselem S. and Beigon A., (1997) Clinical Pharmacokinetics of escalating i.v. doses of dexanabinol (HU–211), a neuroprotectant agent, in normal volunteers. *Intl J of Clinical Pharmacol and Ther* 35, pp. 361–365.

Bar–Joseph A., Berkovitch Y., Adamchik J.and Biegon A., (1994) Neuroprotective Activity of HU–211, a Novel NMDA Antagonist, in Global Ischemia in Gerbils. *Molecular and Chemical Neuropathology* 23, pp. 125–135.

Gallily R., Yamin A., Waksmann Y., Ovadia H., Weidenfeld J., Bar–Joseph A., Biegon A., Mechoulam R. and Shohami E. (1997) Protection Against Septic Shock and Suppression of Tumor Mecrosis Factor and Nitric Oxide Production by Dexanabinol (HU–211), a Nonpsychotropic Cannabinoid. *J of Pharmacol and Exp Ther* 283, pp. 918–924.

Eshhar N., Striem S., Kohen R., Tirosh O. and Biegon A. (1995) Neuroprotective and antioxidant activities of HU–211, a novel NMDA receptor antagonist. *Eur J Pharmacol* 283, pp. 19–29.

Eshhar N., Striem S. and Biegon A., (1993) HU–211, a non–psychotropic cannabinoid, rescues cortical neurones from excitatory amino acid toxicity in culture. *NeuroReport* 5, pp. 237–240.

Biegon A., and Bar Joseph A. (1995) Development of HU211 as a neuroprotectant for ischemic brain damage. *Neurol Res* 17, pp. 275–280.

* cited by examiner

Primary Examiner—Theodore J. Criares
Assistant Examiner—Jennifer Kim
(74) Attorney, Agent, or Firm—Elizabeth Arwine

(57) ABSTRACT

A method of reducing brain damage resulting from seizures caused by an organophosphorus nerve agent includes administering to a patient a therapeutically effective amount of HU-211. The organophosphorus nerve agent may be GB (sarin), GD (soman), GA (tabun) or GF. The therapeutically effective amount of HU-211 is in the range of about 48 mg to about 200 mg per day.

12 Claims, 2 Drawing Sheets

(1 of 2 Drawing Sheet(s) Filed in Color)

METHOD OF REDUCING BRAIN DAMAGE RESULTING FROM SEIZURES

RELATED APPLICATIONS

This application claims the benefit of priority from U.S. provisional patent application Ser. No. 60/155,774 filed Sep. 27, 1999, which is hereby incorporated by reference.

BACKGROUND OF THE INVENTION

The present invention relates in general to reducing brain damage resulting from seizures and in particular to reducing brain damage resulting from seizures caused by nerve agents.

One aspect of chemical warfare involves exposing the enemy to nerve agents. The best defense to nerve agent exposure is, of course, to prevent the soldier from being exposed to the nerve agent. However, exposure to nerve agents may occur and must be treated. Certain nerve agents cause seizures. Examples of organophosphorus nerve agents that cause seizures are GB (sarin), GD (soman), GA (tabun) and GF. It cannot be certain that every victim on the chemical battlefield will receive the fielded therapy regimen (atropine, 2-PAM, diazepam) within the prescribed window of opportunity. These victims may experience prolonged seizure episodes lasting one or more hours. Availability of a drug that will stop development of the lesions after prolonged seizure epilectus would be a valuable adjunct to the current therapeutic regimens.

Throughout the specification, certain publications are identified parenthetically by author and date. A complete identification of these publications is given at the end of the specification. The publication entitled "Neuroprotective Effects of HU-211 on Brain Damage Resulting from Soman-induced Seizures" by Filbert, M. G.; Forster, J. S.; Smith, C. D.; Ballough, G. P.; Army Medical Research Institute of Chemical Defense, Aberdeen Proving Ground, MD, Oct. 1998, is hereby expressly incorporated by reference. Exposure to high concentrations of the nerve agent soman (pinacolylymethylphosphonofluoridate), an organophosphorus (OP) inhibitor of cholinesterases, leads to the development of seizures (Taylor, 1985) and brain damage (Shih and McDonough, 1997; Ballough el al. 1998). Seizure-related brain damage (SRBD) resulting from exposure to soman is considered to be excitotoxic (Olney et al., 1983). Soman-induced seizures are initiated by the high levels of acetylcholine that accumulate as a result of the irreversible inhibition of acetylcholinesterase (AChE). As the duration of seizures increases, excitatory amino acids released by elevated levels of acetylcholine assume control over the seizures and are maintained by this neurotransmitter system (Shih and McDonough, 1997; Olney et al., 1983; Sparenborg et al., 1992). This conclusion is supported by studies demonstrating that soman-induced seizures and the resulting brain damage can be ameliorated by administration of antagonists of N-methyl-D-aspartate (NMDA) such as MK-801 (Braitman and Sparenborg, 1989; Clifford et al., 1989, 1990). Because MK-801 produces neurotoxic effects (Fix et al., 1993), it is not likely to be useful clinically. Therefore, a need exists for a clinically useful neuroprotectant to reduce brain damage caused by organophosphorus nerve agent-induced seizures.

HU-211 (dexanabinol, (+)-(3S,4S)-7-hydroxy-$\Delta$-6 tetrahydro cannabinol 1,1 dimethylheptyl) is a nonpsychotropic cannabinoid that has been shown to have neuroprotectant effects in neurons exposed to excitotoxins in culture (Eshhar et al., 1993, 1995). HU-211 antagonizes glutamatergic neurotransmission in the brain and also inhibits metabolic events that lead to neuronal degeneration (Biegon and Bar Joseph, 1995; Shohami et al., 1997). In addition to having NMDA-blocking activity, HU-211 appears to act as a potent scavenger of peroxy and hydroxy radicals (Shohami et al., 1997) and to reduce the destabilization of calcium homeostasis (Nadler et al., 1995; Striem et al., 1996). HU-211 has been evaluated as a neuroprotectant in animal models of closed head injury, optic nerve crush, and global or focal ischemia. In these models, a single injection of HU-211 given after the insult conferred significant increases in neuronal survival. It is currently being evaluated in phase 1 clinical trials (Biegon, 1998, personal communication). The present invention is a new use for HU-211. The new use is to reduce brain damage resulting from seizures caused by organophosphorus nerve agents.

SUMMARY OF THE INVENTION

It is an object of the present invention to provide a method for reducing seizure-related brain damage caused by organophosphorus nerve agents.

This and other objects of the invention are achieved by a method of reducing brain damage resulting from seizures caused by an organophosphorus nerve agent comprising administering to a patient a therapeutically effective amount of HU-211.

In some embodiments, the organophosphorus nerve agent is one of GB (sarin), GD (soman), GA (tabun) and GF.

Preferably, the therapeutically effective amount of HU-211 is in the range of about 48 mg to about 200 mg per day.

Further objects, features and advantages of the invention will become apparent from the following detailed description taken in conjunction with the following drawing.

BRIEF DESCRIPTION OF THE DRAWING

The file of this patent contains at least one drawing executed in color. Copies of this patent with color drawing(s) will be provided by the Patent and Trademark Office upon request and payment of the necessary fee.

DETAILED DESCRIPTION OF THE PREFERRED EMBODIMENTS

METHODS

Animals

Figure 1A:
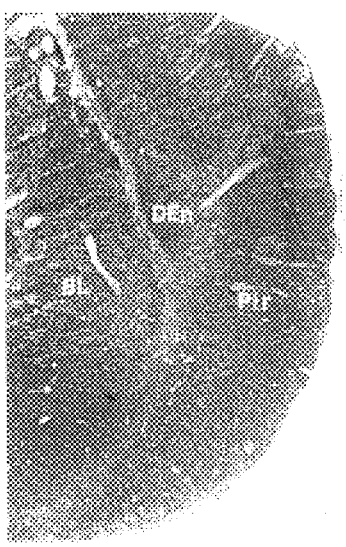
FIGS. 1A–C are MAP2 immunohistochemical stains of the temporal lobes of rats.

Thirty-four male Sprague-Dawley rats (CRL: CD[SD]-BR; Charles River Labs, Wilmington, Mass.), weighing between 250–300 g, were used. Animals were housed individually in polycarbonate cages under conditions of constant temperature ($21\pm2°$ C.) and humidity ($50\pm10\%$) using at least 10 complete air changes per hour of 100% fresh air, and a 12-hour light-dark cycle (full spectrum lighting cycle with no twilight). Throughout the study, food and water were available ad libitum, except during the observation period, which began 1.5 hours prior to and ended 5 hours following soman administration.

Surgeries

Each rat was anesthetized with sodium pentobarbital (55 mg/kg, i.p.) and positioned in a stereotaxic apparatus (David Koif Instruments, Tujunga, Calif.). Three holes were drilled through the skull into which screw electrodes were placed, in accordance with the procedure recommended by Braitman and Sparenborg (1989) for electrocorticographic (ECOG) recordings. Electrodes were connected to a standard small-animal head-piece and secured by dental cement.

Drug Administration and Electrocorticographic Recordings

On the morning of the sixth day following surgeries, animals were connected to an ECoG recording system and allowed at least two hours to acclimate. Baseline ECoG activity and behavior were monitored for at least 15 min. Following baseline recordings, animals were injected (i.p.) with 125 mg/kg of the oxime HI-6. This was followed 30 min later by injection of 180 $\mu$g/kg soman (1.6 $LD_{50}$ s.c.) or sterile saline. Within one min following soman or saline injection, animals were injected (i.m.) with 2 mg/kg atropine methylnitrate (AMN). HI-6 and AMN were administered to protect against the peripheral effects of soman. The treatment drug, HU-211 (Pharmos Ltd., Rehovot, Israel), was injected (25 mg/kg, i.p.) 5 min following the onset of seizures, as determined by ECoG recordings. A non-soman, treatment drug control group received HI-6, saline, AMN, as described above; in addition, HU-211 was administered 15 min following saline injection. The above paradigm yielded five treatment groups: (1) soman-injected positive controls, n=13; (2) HU-211 5 min post-onset, n=8; (3) HU-211 treatment drug controls, n=3; (4) non-soman negative controls, n=6. ECoG recordings were monitored for 5 hours following soman administration. Additional recordings (30 min) were obtained at 24 hours from surviving, animals.

Tissue Processing

Twenty-seven hours after soman/saline administration, rats were given a lethal injection of pentobarbital anesthesia (100 mg/kg, i.p.) and euthanatized, upon evidence of labored breathing, via transcardial perfusion with ice cold 4% paraformaldehyde in 0.1M phosphate buffer (PB, pH 7.4). Brains were immediately excised and longitudinally divided into left and right hemispheres. Alternate hemispheres (left or right) were postfixed by immersion in a second solution of ice cold 4% paraformaldehyde in 0.1M PB for 4–6 hours. These hemispheres were subsequently sucrose-saturated (30% sucrose in 0.1M PB, for 72 hours) and coronally sectioned at 40 $\mu$m. Serial sections either were collected directly onto polylysine coated slides for cresyl violet (CV) staining or cryoprotected (Watson et al., 1986) and stored at −20° C. pending immunocytochemical staining. The remaining hemispheres were paraffin processed, sectioned at 4 $\mu$m and stained with hematoxylin and eosin (H&E).

MAP2 Immunocytochemistry

Immunocytochemistry requires strict attention to detail to achieve uniform staining at sufficient quality for semiquantitation and between-subject comparisons. This procedure employed a monoclonal antiserum, raised in mice, against microtubule-associated protein 2 (MAP2) (Sigma Chemical Co., St Louis, Mo.), and utilized the avidin-biotin-peroxidase method of Hsu et al. (1981); "Elite ABC Mouse Kits" were obtained from Vector Labs (Burlingame, Calif.). For each subject, a single free-floating brain section (bregma −3.1±0.2 and −4.8±0.2 mm) was removed from cryoprotectant and processed simultaneously, with neuroanatomically homologous brain sections from the other subjects, to minimize individual variations associated with tissue processing. Sections were cleared of cryoprotectant solution by four rinses in 0.1M phosphate buffer (PB; pH 7.4; 15 min/rinse, with the exception of the first rinse which lasted 10–45 min). Starting with the second rinse in PB, all incubation times were strictly monitored to ensure uniformity. Endogenous peroxidase activity was quenched by placing sections into 3% $H_2O_2$ in 0.05M Tris buffer (TB; pH 7.6) for 5 min. All of the following steps were preceded by three rinses in 0.05M TB (pH 7.6) unless otherwise indicated. To block nonspecific staining, sections were incubated in 0.05M TB containing 5% normal horse serum and 0.1M D,L-lysine. Sections were incubated for 18 hours at 4° C. in primary antiserum diluted 1:4000 for MAP2 with 0.05M TB containing 1% normal horse serum. Sections were incubated for 30 min at room temperature in biotinylated secondary antiserum (i.e., horse-antimouse) diluted 1:200 in 0.05M TB containing 1% normal horse serum and 1% normal rat serum. Sections were incubated in a solution containing the avidin-biotin peroxidasc complex (diluted 1:50 in 0.05M TB) for 20 min. Each pair of sections was preincubated in 1.0 ml of freshly prepared (i.e., 20–25 min old) 0.05% 3',3-diaminobenzidine tetrahydrochloride (DAB; Sigma Chemical Co., St Louis, Mo.) solution for 5 min, at which time 33 $\mu$l of 0.3% $H_2O_2$ was added and immediately followed by vigorous agitation. Sections remained in the resultant solution containing 0.048% DAB and 0.01% $H_2O_2$ for 2.5 min±3 sec. The reaction was stopped by two rinses in 0.05M TB (for 5 and 15 min, respectively). Negative control sections were incubated in the same solutions for the same incubation times as the other brain sections, with the exception that the primary antibody solution (anti-MAP2 or anti-GFAP) was replaced by a 0.05M TB solution containing 1% horse serum without the primary antibody. Sections were floated onto polylysine-coated slides, dried, dehydrated, cleared and mounted.

MAP2 Image Analysis

Morphometric image analysis of MAP2 immunohistochemistry was performed using a Quantimet 600 Image Analysis System (Leica Cambridge Ltd., Cambridge, England), equipped with an Olympus BH-2 Biological Microscope (Olympus Optical Co., Ltd., Tokyo, Japan). Morphometric assessments of the cross-sectional areas of MAP2-negative staining (i.e., necrosis [Ballough et al., 1995; Hicks et al., 1995]) in the piriform temporal lobe, i.e., piriform cortex and contiguous brain regions (e.g., endopiriform nuclei, amygdaloid nuclei and perirhinal cortex), were performed according to the procedure of Ballough et al. (1995). Previous studies have shown that the deep piriform cortex and surrounding areas present the most clearly defined and easily quantifiable lesions of contiguous necrosis at 27 h following soman-induce seizures in rats (Ballough et al., 1995). To standardize image comparisons between brain sections from each subject, the image analysis system was arbitrarily preset, by adjusting the hue, saturation and intensity of the binary image, to reflect a maximum contrast between MAP2-negative (necrotic) and MAP2-positive immunostaining on a typical soman-injected positive control section. For each brain section, piriform cortical MAP2-negative immunostaining was interactively outlined, using a pointing device, and area determinations were calculated automatically by the image analysis system. The average of two measurements for each brain section was recorded.

H&E Pathological Assessments

H&E stained brain sections (bregma −3.3±0.2 and −4.8±0.2 mm) were assessed for classical histopathological damage to the piriform cortex, amygdaloid complex, hippocampus and thalamus. Damage was scored on a scale of 0 to 4, where 0=no histologic lesion, 1=minimal damage (1–10% neuronal loss), 2=mild (11–25% neuronal loss), 3=moderate (26–45% neuronal loss), and 4=severe (>45% neuronal loss).

Statistical Analysis

For each brain region and each subject, MAP2-negative area measurements were grouped according to treatment and compared using one-way analysis of variance (ANOVA). In all cases, when the one-way ANOVA F-test demonstrated significant differences between group means, the data were further analyzed using the Student-Newman-Keuls (SNK) multiple range test. Regional damage ratings obtained from H&E-stained contralateral hemispheres were assessed using Kruskal-Wallis and Mann-Whitney nonparametric statistical analyses. In all cases, values for p<0.05 were considered significant.

RESULTS

Seizures and Convulsions

All rats that received soman showed ECoG evidence of sustained seizures and status epilepticus for several hours, as defined by the continued presence of high amplitude (i.e., greater than four-times baseline) rhythmic spike or sharp wave activity. Treatment with HU-211 had no detectable effect on the strength or duration of seizures, as determined from visual observation of the ECoG recordings. Band spectral analysis of the ECoG data should provide evidence of whether HU-211 administration produced a less obvious shift in wave pattern. Proconvulsive behavioral signs of soman intoxication included repetitive chewing, facial clonus, forepaw clonus, motor stereotypy, and wet-dog shakes. Overt motor convulsions were characterized by rhythmic clonic jerks of both head and forepaws, rearing, salivation and Straub tail. By all appearances, HU-211 had no effect on proconvulsive or convulsive behavior. Four rats from the soman-injected positive control group and one from the HU-211 five-min post-onset group died prior to scheduled sacrifice and were deleted from the experiment.

MAP2 Immunostaining

Figure 1B:
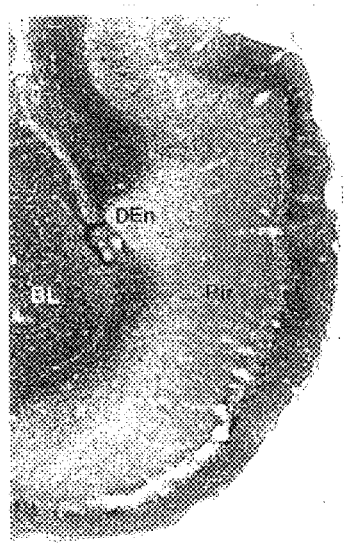
Figure 1C:
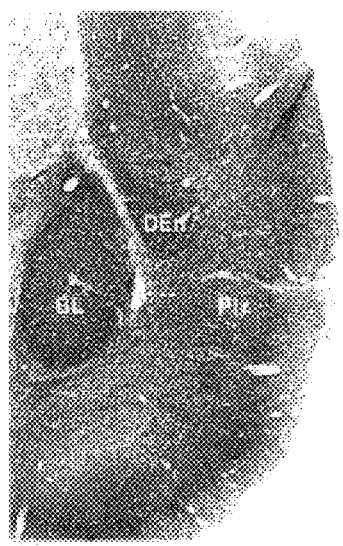

FIGS. 1A–C are MAP2 immunohistochemical stains of the rat temporal lobe showing macroscopic lesions produced by soman and neuroprotection by treatment with HU-211 at 5 minutes following onset of seizures. FIG. 1A is a non-soman control. FIG. 1B shows soman-induced lesions after status epilepticus (SE). FIG. 1C shows neuroprotection produced by HU-211 at 5 minutes following seizure onset, coincident with SE. In FIGS. 1A–C, BL denotes basal lateral amygdala, DEn denotes dorsal endopiriform nucleus and Pir denotes piriform cortex. The black letters indicate damaged areas.

In unlesioned brain regions, MAP2-immunopositive staining was localized in neuronal perikarya, proximal dendrites and neuropil (FIG. 1A). It was not observed in areas composed of white matter except in small numbers of scattered neurons. These findings are consistent with reports by Bernhardt and Matus (1984) and Matus (1994). Immunocytochemical negative control sections for which non-immunized serum was used showed no MAP2 immunoreactivity.

In brain regions exhibiting lesions resulting from soman-induced seizures, pronounced and clearly demarcated reductions in MAP2 immunostaining were observed (FIG. 1B). Severe lesions were typified by a near total absence of MAP2 immunoreactivity. Those brain regions that were most severely affected included the piriform cortex, entorhinal cortex, dorsal endopiriform nucleus and the laterodorsal thalamic nucleus (FIG. 1B). Pronounced reductions in MAP2 immunostaining were often seen in the perirhinal cortex, amygdaloid complex (i.e., lateral, basolateral and posteriolateral cortical amygdaloid nuclei) and midline thalamic nuclei (e.g., mediodorsal and ventromedial). No reductions in MAP2 immunoreactivity were visually discernible in any of the hippocampal fields; however, MAP2 loss was seen in the hilus of the dentate gyrus. In the piriform cortex and contiguous regions, a lesion (i.e., from the soman-injected positive control group) that would be considered typical of those that were morphometrically measured presented the following: with the deep piriform cortex as a central focus, the lateral and ventral margins of the lesion directly abutted, but did not include, the primary olfactory neurons of layer 2. These lesions often extended dorsally to include the perirhinal cortex, and non-contiguous lesions were occasionally seen in the dorsal frontal parietal cortex. Medially, the area of damage consistently included the dorsal endopiriform nucleus and often included the lateral and basolateral amygdala. Necrotic areas devoid of MAP2 immunoreactivity were surrounded by intensified immunostaining in the penumbra, which enhanced the contrast between the penumbra and necrotic border and facilitated delineation (FIG. 1B).

Figure 2:
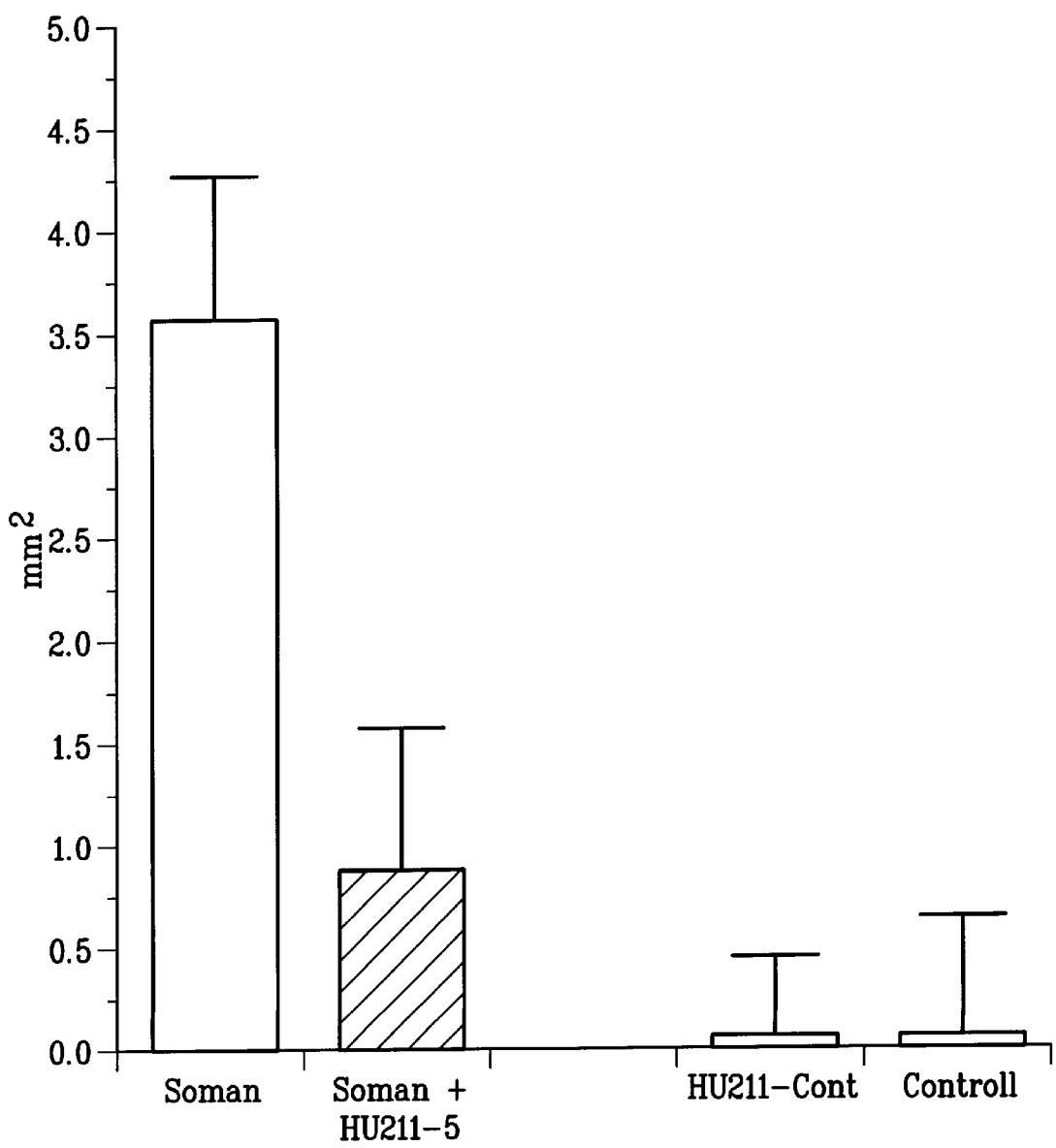
FIG. 2 is a histogram showing cross-sectional areas of temporal lobe necrosis.

Neuroprotection by HU-211, administered 5 min post-onset of seizures, is clearly seen in FIG. 1C. Histograms of mean cross-sectional areas of temporal lobe necrosis (i.e., MAP2-negative immunostaining in the piriform cortex and contiguous regions) are shown in FIG. 2. The cross-sectional area of MAP2-negative immunostaining (necrosis) of the temporal lobes from soman-injected positive controls was $3.56 \pm 0.75$ mm$^2$. HU-211 reduced this necrotic cross-sectional area to $0.86 \pm 0.69$ mm$^2$ (i.e., a 75.8% reduction). The apparent elevation of MAP2 staining seen in FIG. 1C more than likely resulted from mRNA-induced expression of MAP2 during the intense seizure activity (Ballough et al., 1995). Neither the non-soman injected negative control nor the HU-211 drug treatment control groups showed evidence of brain damage as discerned from examination of MAP2-immunostained sections.

H&E Histopathological Assessments

General histopathological assessments of H&E-stained brain sections from rats that received soman but not HU-211 indicated that soman-induced seizure-related brain damage was bilaterally symmetrical and characterized by tissue necrosis, neuronal loss, chromatolysis, vacuolization, pyknosis and gliosis. The most severe brain damage was consistently observed in the piriform cortex, entorhinal cortex, dorsal endopiriform nucleus and the laterodorsal thalamic nucleus. Pronounced damage was often seen in perirhinal cortex, amygdaloid complex (i.e., lateral, basolateral and posteriolateral cortical amygdaloid nuclei), hippocampus (i.e., hippocampal fields CA1 and CA3 and dentate gyrus), and midline thalamic nuclei (e.g., mediodorsal and ventromedial).

Histopathological damage ratings for H&E-stained brain sections are based on the presence of necrotic neurons and/or the absence of a defined neuronal population; shrunken neurons are considered the result of artifactual change. Damage to the neuropil is progressively greater as ratings increase from "mild" to "severe," and is characterized by increasingly severe malacia and hyalinization typical of necrosis.

A statistically significant (p=0.03) drop in damage ratings was observed in the HU-211 group treated at 5 min after onset of seizures ($2.4 \pm 0.38$) compared with soman controls ($3.8 \pm 0.2$). This represents a damage reduction from severe (i.e., from >45% neuronal loss in untreated soman-exposed groups) to mild (11–25% neuronal loss in the HU-211, 5-min group). Damage ratings for HU-211 controls and vehicle controls were all zero.

DISCUSSION

The results presented here are significant in that HU-211 reduced neuronal damage following exposure to soman without stopping established seizures. Earlier reports had indicated that noncompetitive NMDA antagonists such as ketamine and MK-801 protect thalamic neurons from seizure-related brain damage without preventing seizure activity (Labruyere et al., 1986; Smith et al., 1987; Clifford et al., 1989, 1990). It was suggested by these investigators that the NMDA antagonists may have prevented seizure-related damage by blocking NMDA receptor ion channel complexes on the dendrosomal surfaces through which glutamate excitotoxicity is expressed (Clifford et al., 1989). It is also possible that seizure activity in some brain areas can be maintained by other transmitter systems/receptors without NMDA participation (Clifford et al., 1989). In addition to NMDA blocking activity, HU-211 has been reported to block calcium influx and possess free radical scavenging activity (Biegon and Bar Joseph, 1995).

For humans, the active dose of HU-211 to reduce seizure-related brain damage caused by organophosphorus nerve agents is generally in the range of from about 48 mg to about 200 mg per day. However, it is evident to one of skill in the art that dosages would be determined by the attending physician, according to the method of administration, patient's age, weight, counterindications and the like. Administration of therapeutically effective amounts of HU-211 as used herein encompasses oral, parenteral, intravenous, intramuscular, sub-cutaneous, transdermal, intratechal, rectal and intra-nasal administration.

While the invention has been described with reference to certain preferred embodiments, numerous changes, alterations and modifications to the described embodiments are possible without departing from the spirit and scope of the invention as defined in the appended claims, and equivalents thereof.

REFERENCES

Ballough G. P. H., Martin L. J., Cann F. J., Graham J. S., Smith C. D., Kling C. E., Forster J. S., Phann S., and Filbert M. G. (1995) Microtubule-associated protein 2 (MAP2): a sensitive marker of seizure-related brain damage. J. Neurosci. Meth. 61, 23–32.

Ballough G. P. H., Cann F. J., Smith C. D., Forster, J. S., Kling C. E., and Filbert, M. G. (1998) $GM_1$ monosialoganglioside pretreatment protects against soman-induced seizure-related brain damage. Molecular and Chemical Neuropathology 34, 1–23.

Bernhardt R. and Matus A. (1984) Light and electron microscopic studies of the distribution of microtubule-associated protein 2 in rat brain: a difference between dendritic and axonal cytoskeletons, J. Comp. Neurol. 226, 203–221.

Biegon A., and Bar Joseph A. (1995) Development of HU211 as a neuroprotectant for ischemic brain damage. Neurol Res 17, 275–280

Braitman D. J. and Sparenborg S. (1989) MK-801 protects against seizures induced by the cholinesterase inhibitor soman. Brain Res. Bull. 23, 145–148

Clifford D., Zorumski C. and Olney J., (1989) Ketamine and MK-801 prevent degeneration of thalamic neurons induced by focal cortical seizures. Experimental Neurol 105, 272–279.

Clifford D., Olney J., Benz A., Fuller 1., and Zorumski C. (1990) Ketamine, phencyclidine, and MK-801 protect against kainic acid-induced seizure-related brain damage. Epilepsia 31, 382–290.

Eshhar N., Striem S. and Biegon A., (1993) HU-211, a non-psychotropic cannabinoid, rescues cortical neurones from excitatory amino acid toxicity in culture. NeuroReport 5, 237–240.

Eshhar N., Striem S., Kohen R., Tirosh O. Biegon A. (1995) Neuroprotective and antioxidant activities of HU-211, a novel NMDA receptor antagonist. Eur J Pharmacol 283, 19–29

Fix A.S., Horn J. W., Wightman K. A. Johnson C. A., Long G. G., Storts, R. W., Farber N., Wozniak D. F. Olney J. W. (1993) Neuronal vacuolization and necrosis induced by the noncompetitive N-methyl-D-aspartate (NMDA) antagonist MK-801 (dizocilpine maleate): a light and electron microscopic evaluation of the rat retrosplenial cortex. Exp Neurol 123, 204–215.

Hicks R. R. , Smith D. H. and McIntosh T. K. (1995) Temporal response and effects of excitatory amino acid antagonism on microtubule-associated protein 2 immunoreactivity following experimental brain injury in rats. Brain Res 678, 151–160.

Hsu S-M, Raine L., and Fanger H. (1981) Use of avidin-biotin-peroxidase complex (ABC) in immunoperoxidase techniques: a comparison between ABC and unlabeled antibody (PAP) procedures. J Histochem. Cytochem. 29, 577–580.

Labruyere J, Fuller T., Olney J., Price M, Sorumski C. and Clifford D. (1986) dPhencyclidine and ketamine protect against seizure-related brain damage. Neurosci. Abst. 12: 344.

Matus A. (1994) MAP2, in Microtubules, (Hyams J. S. and Lloyd C. W., eds.), Wiley-Liss Inc., New York, NY.

Montgomery D. L. (1994) Astrocytes: Form, Function, and Roles in Disease: Review. Vet. Pathol. 31, 145–167

Nadler V., Biegon A, Beit-Yanni E., Adamchik J and Shohami E., (1995) Ca accumulation in rat brain after closed head injury: attenuation by the novel neuroprotective agent HU-211. Brain Res 685, 1–11.

Olney J. W., de Gubareff T. and Labruyere J. (1983) Seizure-related brain damage induced by cholinergic agents. Nature 301, 520–522.

Shih T-M. and McDonough J. H. (1997) Neurochemical mechanisms in soman-induced seizures. J Applied Toxicol 17: 255–264.

Shohami F, Beit-Yannai E., Horowitz M., and Kohen R. (1997) Oxidative stress in closed-head injury: brain antioxidant capacity as an indicator of functional outcome. J Cereb Blood Flow Metab 17, 1007–1019.

Smith G., Golden G., Reyes P. and Farriello R., (1987) Effects of MK801, an NMDA receptor antagonist, on kainate induced seizures in rats. Soc Neurosci. Abst 13: 1031.

Sparenborg S., Brennecke L. H., Jaax, N. K. and Braitman D. J. (1992) Dizocilpine (MK-801) arrests status epilepticus and prevents brain damage induced by soman. Neuropharmacology 31, 357–368.

Striem S., Lavie V. and Biegon A. (1996) The nonpsychotropic cannabinoid HU-211 rescues hippocampal neurones from b-amyloid induced toxicity. Society for Neuroscience Vol 22, 196.

Taylor P. (1985) Anticholinesterase agents. In The Pharmacological Basis of Therapeutics, $6^{th}$edn, ed. by A. G. Filman, L. S. Goodman, T. W. Rall and F. Murad, pp 110–129, Macmillan, N.Y.

Watson R. E., Wiegand S. J., Clough R. W., and Hoffman G. E. (1986) Use of cryoprotectant to maintain long-term peptide immunoreactivity and tissue morphology. Peptides 7, 155–159.

What is claimed is:

1. A method of reducing brain damage resulting from seizures caused by an organophosphorus nerve agent comprising administering to a patient a therapeutically effective amount of HU-211.

2. The method of claim 1 wherein the organophosphorus nerve agent is one of GB (sarin), GD (soman), GA (tabun) and GF.

3. The method of claim 1 wherein the therapeutically effective amount of HU-211 is in the range of about 48 mg to about 200 mg per day.

4. The method of claim 3 wherein the patient is administered the therapeutically effective amount of HU-211 by oral administration.

5. The method of claim 3 wherein the patient is administered the therapeutically effective amount of HU-211 by parenteral administration.

6. The method of claim 3 wherein the patient is administered the therapeutically effective amount of HU-211 by intravenous administration.

7. The method of claim 3 wherein the patient is administered the therapeutically effective amount of HU-211 by intramuscular administration.

8. The method of claim 3 wherein the patient is administered the therapeutically effective amount of HU-211 by sub-cutaneous administration.

9. The method of claim 3 wherein the patient is administered the therapeutically effective amount of HU-211 by transdermal administration.

10. The method of claim 3 wherein the patient is administered the therapeutically effective amount of HU-211 by intratechal administration.

11. The method of claim 3 wherein the patient is administered the therapeutically effective amount of HU-211 by rectal administration.

12. The method of claim 3 wherein the patient is administered the therapeutically effective amount of HU-211 by intra-nasal administration.

* * * * *